United States Patent [19]

Chek

[11] Patent Number: 5,303,480
[45] Date of Patent: Apr. 19, 1994

[54] CRANIO-CERVICAL SAGITTAL-ALIGNMENT CALIPER AND UNIVERSAL MEASUREMENT SYSTEM

[76] Inventor: Paul W. Chek, 8308 (1-E) Regency Rd., San Diego, Calif. 92122

[21] Appl. No.: 984,230

[22] Filed: Nov. 27, 1992

[51] Int. Cl.$^5$ .......................... A61B 5/103; G01B 5/14
[52] U.S. Cl. ........................................ 33/512; 128/774
[58] Field of Search .................. 33/512, 511, 533, 645, 33/427, 452, 464, 832; 128/774, 777, 781, 782

[56] References Cited

U.S. PATENT DOCUMENTS

| | | |
|---|---|---|
| 2,219,999 | 10/1940 | Mears ................................... 128/774 |
| 3,377,712 | 4/1968 | Farkas et al. .......................... 33/512 |
| 4,530,367 | 7/1985 | Desjardins et al. ................... 128/777 |
| 4,779,349 | 10/1988 | Odensten . |
| 4,802,494 | 2/1989 | Gardiner ................................ 33/512 |

FOREIGN PATENT DOCUMENTS 61594  6/1967  Fed. Rep. of Germany ...... 128/774

*Primary Examiner*—William A. Cuchlinski, Jr.
*Assistant Examiner*—C. W. Fulton
*Attorney, Agent, or Firm*—Inventech

[57] ABSTRACT

A specialized hand-portable device for use by a medical-technician in measuring the amount of head fore-/aft-deviation from a "standardized norm" reference-point (manubrium of sternum). Configured in the form of an inverted T-shape, the vertical body portion of which serves as a common stanchion, including a horizontal lower scale-beam member having a sternal-probe. The vertical stanchion is adjustable fore/aft relative to the chest sternum; the probe's tip entity being shaped to lay naturally against one's sternal-notch. The upper portion of the stanchion includes a vertically adjustable second horizontal-probe member, the tip-rest thereof being formed to lightly impinge upon the zygomatic-arch region of one's face. The instrument is intitially set to "zero" on the sternal/reference-scale, which precalibration adheres to an "ideal norm" of reference, while leveling to a visual sight-bubble. Hence, consistent measurement deviation (to the millimeter) from this pre-established norm, reveals the patient's precise cranial-deviation relative to the fixed manubrium point. Armed with this data, a suitable correctional program may be prescribed and/or monitored to measure progression toward intended satisfactory results.

7 Claims, 1 Drawing Sheet

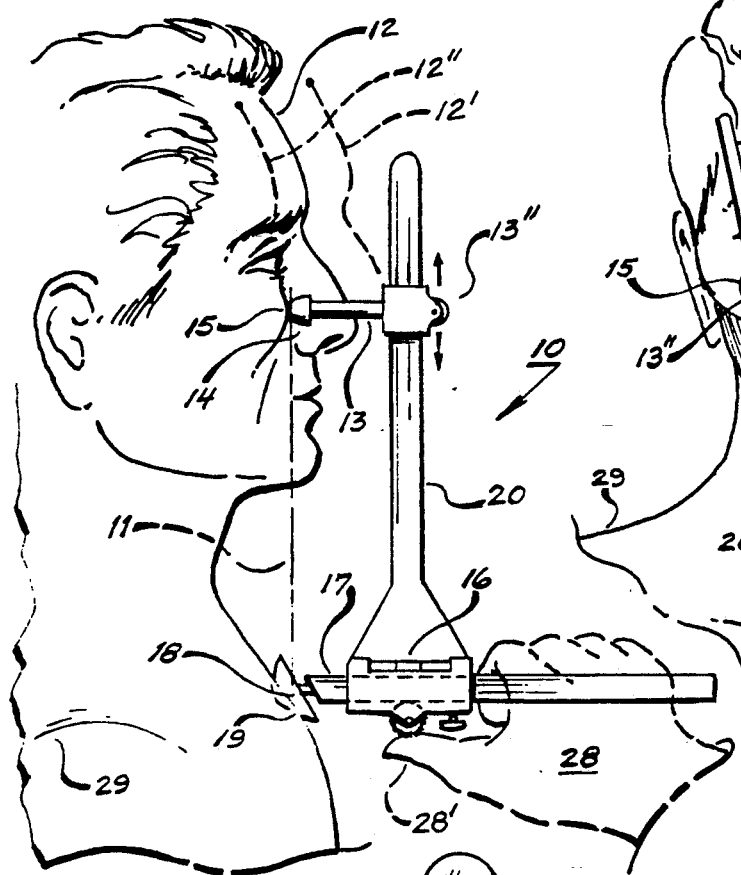
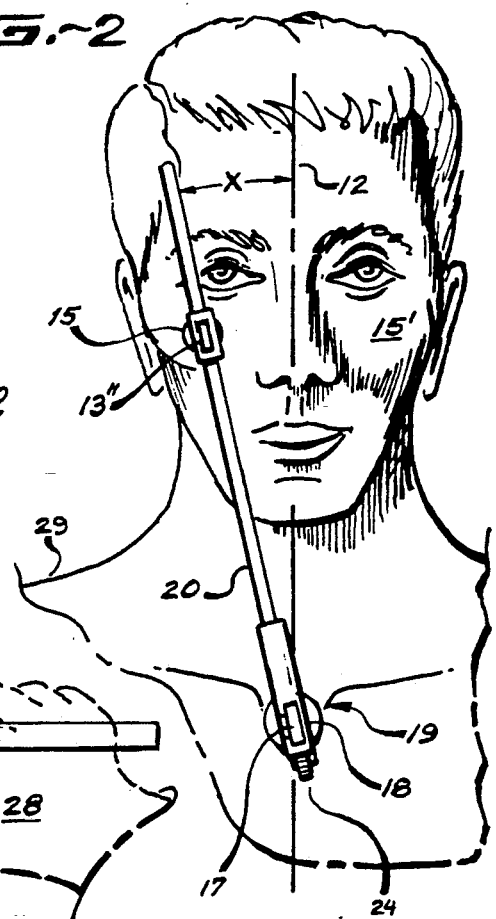
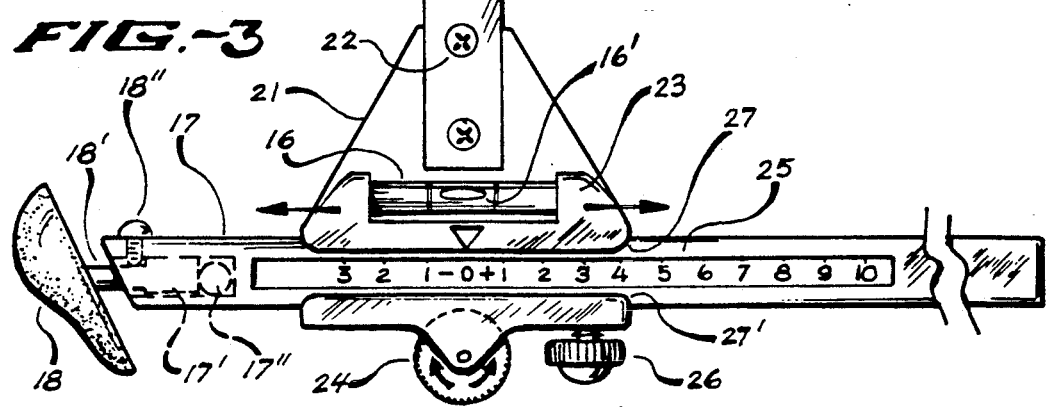

CRANIO-CERVICAL SAGITTAL-ALIGNMENT CALIPER AND UNIVERSAL MEASUREMENT SYSTEM

PROBLEMATICAL BACKGROUND OF RELEVANT EARLIER INVENTION

This invention relates to hand-portable measuring instruments, particularly those calibrated as to facilitate measurement of the human physique, especially as it relates to anatomical or postural stance of an individual, relative to a so called "optimal"(ideal) standard.

Heretofore, human-engineering scientists and physical-therapy technicians have devised various sorts of specialized measuring devices. These have been designed for extrapulating some form of reference-data useful in compiling statistics, either for pure anthropomorphic-studies, or for aiding the rehabilitation of a patient. However, as yet, no hand-portable orthopedic-instrument has been available to conveniently and accurately determine the fore/aft-posture condition of any human specimen.

For example, U.S. Pat. No. 3,955,285(filed—September 1974) sets forth a floor-stand having a fixed vertical stanchion-staff which may be readily adjusted vertically at three separate stations; so as to determine hip, shoulder, and head region reference points. This inventor employed a heel/striker-curb for the patient to backup against, thereby establishing a reliably practical common point of physical-reference. However, their was nothing built-in to the 7½-foot high apparatus which enabled the technician to determine actual presence of Fore/aft "stoop" of a given patient.

Interestingly, in U.S. Pat. No. 4,437,753(filed—March 1981) for a personal camera steadying device, the inventor provides a bipod-legged arrangement which attaches to a popular 35 mm-camera; wherein one of the legs braces against one's shoulder, while the other braces upon one's chest-sternum. However, while the camera eyepiece itself is placed proximal to the zygoma-bone of one's eye bone surround, there is no provision here for attaining any manner of anatomical measurment as shall be subsequently explained. Another camera-stabilizer device is shown in U.S. Pat. No. 3,434,406(filed—January 1966), which features a single supporting-leg that extends aft and down against one's chest-sternum in order to better steady the camera being otherwise held in the operator's hands.

In U.S. Pat. No. 4,425,713 (filed—August 1982) for a postureometer, the inventor provides a base-plate having locative foot-impressions, serving to position the patient at a predetermined location relative to a vertical stanchion. Similar to the first patent mentioned above, the stanchion includes hip, shoulder and head measurement probes; plus, this stanchion also features a series of horizontal-probes readily adjustable from the stanchion, so as to plot the curve of one's spine. However, the apparatus is not hand-portable, and no provision is anticipated for detecting fore-aft head stoop.

Another U.S. Pat. No. 4,779,349 (filed—March 1987) shows a simple hand-portable measuring caliper, capable of reading the between bone parts in a knee-joint, but is relevant only as to the centimeter-calibrated scale and rotary-index adjustment.

A back-incline indicator is set forth in U.S. Pat. No. 4,958,145 (filed—May 1989), which employs a mercury-switch and beeper, thereby enabling a patient to know if they have exceeded a predetermined degree of back-incline (such as may be determined by an Orthopedist). However, there is no provision for determining actual forward stoop of a person, which is different than back-incline, which is induced in the spine rather than from one's bending forward at the hips.

The disclosure of U.S. Pat. No. 5,038,489 (filed—June 1990) shows an inexpensive posture measuring instrument, which is hand-held by the operator while viewing through the paddle-like formation of clear-plastic. Included is a likewise transparent gravity-weighted indicator which pivots freely on an axis central to the paddle face. The arrangement enables the operator to align the inscribed reference-lines on the gravity-weighted pointer with the bridge of the subject's nose for example, while aligning the reference-line inscribed on the hand-held portion with the top of the ear for example; whereupon the paddle is turned so as to obtain a similar reading at the top of the opposite ear. Results of the two readings are compared, and the difference indicates the apparent lateral deviation from the vertical. However, the device serves no purpose when used in side-view or profile of the patient, as does that of the instant invention hereof.

SUMMARY OF THE INVENTION

A. In view of the foregoing discussion about the earlier invention art, it is therefore important to make it clear to others interested in the art that the object of this invention is to provide a special hand-portable measuring-caliper, designed to be held by an orthopedist or chiropractor who positions the device relative to a patient's head and chest, so as to obtain a reliable index reading as to possible anatomical-deviation of the patient's side-profile (sagittal-plane) posture relative to a known desired healthy optimal anatomical-standard reading;—through serial use of the instrument upon a wide percentile-range of healthy specimens. The results of this newly derived data, is not only immediately indicative of a possible need for remedial treatment of the patient, but it is also valuable in charting progressional reference-data, as the patient is being administered appropriate treatment corrective of the originally detected sagittal deviation.

B. Another object of this invention is to provide an anatomical measuring-caliper based upon the inventor's discovery as to a relationship between the fore/aft disposition of a person's zygomatic-arch prominence, and the prominence of one's sternal-notch, and a constant level (vertical/horizontal) plane of orientation regardless as to one's position in azimuth. The inventor has found that a very reliable anatomical correlation exists between the two identified bonny prominences, such that virtually any therapy-technician can readily identify and reveal to a patient the exact condition of one's upper-torso region posture. This important anatomical testing-procedure is gaining in favor by professionals, as to now being referred to as the "Chek-point" in deference to the inventor, since it also eludes in double-entendre to the notion of being able to quickly obtain a reading from the patient, and to then generally reveal this condition (good or bad) to the patient. This direct evidence is found to greatly aid the professional practitioner in procedure. Additionally, the instrument hereof can be relied upon as an international-standard in demonstrating any comparative progress in reducing slight to serious sagital-deviation, as result of corrective procedure administered over the course of weeks, months, or years.

C. Another object of this invention, is to provide a relatively inexpensive and light-weight anatomical measuring-caliper which is at once both simple in construction and operation; preferably comprising only three primary component parts. The main structural member is a uniting vertical stanchion like I-beam serving as the primary component supporting both a vertically adjustable zygoma-bone/horizontal-probe, which includes no reference measuring-scale; and a horizontally adjustable sternal-bone/horizontal-probe which includes a sagittal-deviation reference-scale(bearing indicia inscribed in C.M.'s) pointed to by a fixed-indicator stationed upon the base of the translatable stanchion. Vital to the accurate operation of the instrument is a substantially conventional bubble type sighting-level member, preferably built-in to the base portion of the stanchion. While a weighted gravity-type indicator could be employed as an alternate leveling device, it is a potential source of malfunction via frictional binding, since such mechanism necessarily dependant upon a free-pivoting action.

DESCRIPTION OF THE PREFERRED EMBODIMENT DRAWINGS

The foregoing and still other objects of this invention will become fully apparent, along with various advantages and features of novelty residing in the present embodiments, from study of the following description of the variant generic species embodiments and study of the ensuing description of these embodiments. Wherein indicia of reference are shown to match related points given in the text, as well as the claims section annexed hereto; and accordingly, a better understanding of the invention and the variant uses is intended, by reference to the drawings, which are considered as primarily exemplary and not to be therefore construed as restrictive in nature.

FIG. 1, is a left side sagittal elevation-view showing an exemplified use of the invention with a human subject, including the operator's right-hand shown in phantom outline for greater clarity.

FIG. 2, is a frontal elevation-view thereof, including a vertical center reference-line demonstrating the normal declination of the instrument during the measuring procedure.

FIG. 3, is an enlarged detail view of the invention as revealed in FIG. 1.

ITEMIZED NONMENCLATURE REFERENCES:

10—the overall invention
11—vertical plumb phantom ref-line
12,12',12"—human-profile phantom zero/ref.-line, neg.-/ref.-line, pos./ref.-line
13—upper/zagomatic-probe
14—probe tip-rest
15—human zagomatic-arch
16,16'—visual sighting-tube level, internal-bubble
17,17',17"—lower measuring-beam, axle-bore, thrust-ball
18,18',18"—sternal-probe tip, intermediate pivot-axis, retention-screw
19—human sternal-notch
20—vertical stanchion-beam
21—lower stanchion bracing
22—stanchion assembly screws
23—stanchion level mounting
24—stanchion thumb-wheel
25—metric measuring scale
26—stanchion thumb-lock
27,27'—C-section slider-rail upper, lower
28,28'—operator's hand, thumb
29—specimen's shoulder reference

DETAILED DESCRIPTION OF THE PREFERRED EMBODIMENTS

Initial reference is given by way of FIG. 1, wherein is exhibited the overall invention 10, as it basically appears while being held by hand 28 in place relative to an exemplified human profile representation 12. Note here, how the horizontal upper/zagomatic-probe member 13 has been first adjusted vertically so that the foremost tip-rest portion 14 thereof only lightly impinges upon the zigomatic-arch 15 region of the specimen's cheekbone. At this time, the vertical interval between the upper probe-tip 14 and the lower sternal-probe tip 18 is adjusted via thumb-wheel 13" to the physical size of the individual specimen. While maintaining the instrument at the critical upper reference location 15, the operator carefully observes the visual sighting-bubble 16, while gently adjusting the lower horizontal scale-beam 17 fore/aft so that the sternal-probe tip member 18 just impinges upon specimen's sternal-notch region 19, whilst the visual leveling device indicates the instrument's beam 17 to be precisely leveled. Since the vertical stanchion member 20 is made rigidly perpendicular while longitudinally translatable relative to the beam 17, the only angularity involved is revealed in FIG. 2, wherein the stanchion is tilted to the left(or right) here only about 13-degrees at arrowed reference-X(relative profile station 12), as to enable impingement with specimen's cheek-bone region 15. Notice how sternal-probe tip 18 remains resting gently supported upon the sternal-notch 19 of specimen's chest sternum, regardless as to oblique tilt to the left or right, the sternal-probe being preferably mounted to the beam 17 via an intermediate tilt-axis(or equivalent) axial-coupling arrangement 18', preferably having free pivotal action limited to approximately 20-degrees either direction from vertical;—thereby serving to eliminate twisting of the tip 18 relative to application against specimen's sternal-notch skin region 19. The axis 18' is freely supported within beam support-bore 17', and may be aided by low-friction thrust-ball 17", while keyed in place by means of retention-screw 18" which acts against tilt-limit flat-stops on the axis below. In FIG. 3, the vital reading obtained upon the sagittal/reference-scale 25 corresponds to the relative deviation attained by virtue of the specimen's individual sagittal-alignment being revealed such as via the phantom reference-line 11, which is an imaginary forwardly prominent surface of the zigomatic-arch 15 above, and the sternal-notch 19 below. Here, we find exemplified a substantially ideal sagittal-alignment representation; while by way of further reference demonstration, a common positive sagittal-reading is exhibited along the specimen phanton-outline profile line 12', while the opposite and less common deviation example would be found exemplified via phantom-outline profile line 12". Such deviation readings typically range from only 0-3 cm's(negative) for sagittal-profile line 12", while a more pronounced positive deviation reading of 0-10 cm's is to be found in the sagittal-profile condition referenced line 12'.

Extensive tests have been objectively conducted among specimens seated in their natural head-forward posture position, by qualified medical practitioners utilizing a Chek/Sagittal-posture Caliper device configured substantially as exemplified in the referenced Figures. The extrapulated sagittal-reading data has provided a remarkable intertester(multipul users) data reliability-factor variance of less than 1-cm./maximum and 2-cm./minimum. These results have demonstrated to observers that this new instrument will precipitate a much improved table of orthopedic knowledge in the form of sagittal reference-data, enabling medical-practitioners to better determine the scope of treatment when eventually compared to an international collective body of; wherein are given consistantly reliable sagittal-deviation data, and showing exactly how patients responded to various forms of correctional treatment. Such reliable data, will ultimately reveal which form of treatment is best for a given sagittal-deviation condition.

Therefore, it is understood that the utility of the foregoing adaptations of this invention are not necessarily dependent upon any prevailing invention patent; and while the present invention has been well described hereinbefore by way of preferred embodiments, it is to be realized that various changes, alterations, rearrangements, and obvious modifications may be resorted to by those skilled in the art to which it relates, without substantially departing from the implied spirit and scope of the instant invention. Therefore, the invention has been disclosed herein by way of example, and not as imposed limitation. Accordingly, the embodiments of the invention in which an exclusive property or proprietary privilege is

What is claimed of proprietary inventive origin is:

1. An inverted-T shaped anatomical caliper device, capable of measuring for possible sagittal cranio-cervical alignment deviation exhibited by any given human specimen, whereby a standardized technique is conveniently and accurately facilitated for determining critical cranio posture relative to said specimen's manubrium, simply by reading a display-scale; comprising:
   a. a vertical stanchion member, serving as a common uniting structural element;
   b. a built-in precision leveling means;
   c. an upper/zygomatic-probe member, having adjustable means by which to be vertically translated relative to said stantion member;
   d. a lower/sternal-probe beam like member, having adjustable means by which to be longitudinally translated relative to said stantion member, including a sagittal-deviation readout-scale fixedly arranged thereto;
   e. a sagittal-deviation readout-pointer fixedly arranged at the base of said stantion member, thereby facilitating visual readout of a reference measurement scale affixed to said lower/sternal-probe beam member.

2. An anatomical sagittal measuring instrument according to claim 1, wherein said vertical stanchion member includes a lower-guide means enabling said vertical stanchion member to translate along said lower-guide so as to obtain readjustment to a given said specimen's particular sagittal measurement setting, including a manual position-lock means thereto.

3. An anatomical sagittal measuring instrument according to claim 1, wherein the outermost end of said sternal-probe member includes a sternal-rest entity formed to lay upon the superior anterior surface of said specimen's manubrium, said sternal-rest member including a sternal-node entity thereto formed to positively detent into said specimen's sternal-notch.

4. An anatomical sagittal measuring instrument according to claim 1, wherein said sternal-rest member is provided with a longitudinal pivot-axis enabling said sternal-probe and stanchion aggregation to rotate aproximately 30-degrees without moving the sternal-rest upon patient's sternum.

5. An anatomical sagittal measuring instrument according to claim 1, wherein said built-in leveling means is a conventional bubble-level sighting device.

6. An anatomical sagittal measuring instrument according to claim 3, wherein said sternal-rest member has a free pivotal axis mounting longitudinally into said sternal-probe beam end, including means limiting said pivotal action to approximately 30-degrees each direction from the vertical.

7. A standardized system for universal anatomical measurement of human speciments, to determine individual cranio-cervical sagittal posture condition; comprising:
   a. locating the zygomatic-arch prominence of said specimen;
   b. locating the sternal-notch manubium of said specimen;
   c. projecting a vertical reference-line between both said locations a. and b., then measuring the horizontal longitudinal interval between these two points;
   d. utilizing said interval measurement of procedure c., extrapolate the amount of possible sagittal deviation exhibited by said specimen.

* * * * *